United States Patent
Goldstein et al.

(10) Patent No.: US 11,351,397 B2
(45) Date of Patent: Jun. 7, 2022

(54) APPARATUS FOR TREATING A TARGET SITE OF A BODY

(71) Applicant: TEL HASHOMER MEDICAL RESEARCH, INFRASTRUCTURE AND SERVICES LTD., Ramat Gan (IL)

(72) Inventors: Jeffrey Goldstein, Herzeliya (IL); Nir Peled, Hod Hasharon (IL); Zvi Symon, Jerusalem (IL)

(73) Assignee: Tel Hashomer Medical Research, Infrastructure and Services Ltd., Ramat Gan (IL)

(*) Notice: Subject to any disclaimer, the term of this patent is extended or adjusted under 35 U.S.C. 154(b) by 607 days.

(21) Appl. No.: 15/030,878

(22) PCT Filed: Oct. 22, 2014

(86) PCT No.: PCT/IB2014/065532
§ 371 (c)(1),
(2) Date: Apr. 21, 2016

(87) PCT Pub. No.: WO2015/059646
PCT Pub. Date: Apr. 30, 2015

(65) Prior Publication Data
US 2016/0256710 A1 Sep. 8, 2016

Related U.S. Application Data

(60) Provisional application No. 62/016,670, filed on Jun. 25, 2014, provisional application No. 61/961,731, filed on Oct. 22, 2013.

(51) Int. Cl.
*A61N 5/10* (2006.01)
*A61B 10/02* (2006.01)
(Continued)

(52) U.S. Cl.
CPC ............ *A61N 5/1037* (2013.01); *A61B 10/02* (2013.01); *A61B 18/1492* (2013.01);
(Continued)

(58) Field of Classification Search
CPC .. A61N 5/1037; A61N 5/1048; A61N 5/1049; A61N 5/1064; A61N 5/1065; A61N 5/1068; A61N 5/1067
See application file for complete search history.

(56) References Cited

U.S. PATENT DOCUMENTS 6,597,939 B1 * 7/2003 Lampotang ............ A61B 6/541
128/202.13
7,393,329 B1 * 7/2008 Wong .................. A61M 16/024
600/534
(Continued)

FOREIGN PATENT DOCUMENTS

WO 9942034 8/1999

OTHER PUBLICATIONS

International Search Report dated Feb. 5, 2015 for International Application No. PCT/IB2014/065532 filed Oct. 22, 2014.

*Primary Examiner* — Carrie R Dorna
(74) *Attorney, Agent, or Firm* — A.C. Entis-IP Ltd.; Allan C. Entis

(57) ABSTRACT

Apparatus for performing a procedure at a target site of a patient's body, the apparatus comprising: a continuous positive airway pressure (CPAP) apparatus that provides CPAP to the patient's lungs; a medical device for performing the procedure at the target site; and a controller that controls the CPAP apparatus to provide CPAP to the patient's lungs during performance of the procedure.

12 Claims, 3 Drawing Sheets

(51) Int. Cl.
*A61B 18/14* (2006.01)
*A61B 6/00* (2006.01)
*A61N 7/00* (2006.01)
*A61M 16/10* (2006.01)
*A61M 16/06* (2006.01)
*A61B 18/00* (2006.01)

(52) U.S. Cl.
CPC ........... *A61M 16/10* (2013.01); *A61N 5/1049* (2013.01); *A61N 7/00* (2013.01); *A61B 6/5217* (2013.01); *A61B 6/5264* (2013.01); *A61B 2018/00577* (2013.01); *A61M 16/06* (2013.01); *A61M 16/0683* (2013.01); *A61N 5/1067* (2013.01)

(56) References Cited

U.S. PATENT DOCUMENTS

| | | | |
|---|---|---|---|
| 2005/0229926 A1 | 10/2005 | Fink et al. | |
| 2010/0286544 A1 | 11/2010 | Tanaka et al. | |
| 2010/0294279 A1 | 11/2010 | Tonascu et al. | |
| 2013/0116555 A1* | 5/2013 | Kuzelka | A61B 6/03 600/427 |
| 2014/0066749 A1* | 3/2014 | Dickerson | A61B 5/7285 600/413 |

* cited by examiner

APPARATUS FOR TREATING A TARGET SITE OF A BODY

RELATED APPLICATIONS

The present application is a U.S. National Phase of PCT/IB2014/065532 filed on Oct. 22, 2014, which claims the benefit under 35 U.S.C. 119(e) of U.S. Provisional Application 61/961,731 filed on Oct. 22, 2013 and U.S. Provisional Application 62/016,670 filed on Jun. 25, 2014. The contents and disclosures of these prior applications are incorporated herein by reference in their entirety.

TECHNICAL FIELD

Embodiments of the invention relate to treating a target site in a patient.

BACKGROUND

Various methods of treating patients with different types of radiation have matured since E. O. Lawrence first used neutron radiation to cure his mother of cancer in 1932, and R. R. Wilson first suggested using protons to treat cancer in a seminal paper in 1946. Today, most medical centers have, or have access to, at least one facility for generating a radiation beam for treating malignancies. The facility generally comprises an accelerator for accelerating a beam of charged particles, for example electrons or protons, a target with which the beam collides to produce a desired type of radiation, and apparatus for accurately aiming the desired radiation as a well defined therapeutic radiation beam at a target site of a malignancy in a patient's body. The radiation beam may be a particle beam of electrons, a beam of hadrons, such as protons, neutrons, or alpha particles, or a beam of electromagnetic radiation, such as X-rays or gamma rays.

Therapeutic radiation beams operate to kill malignant cells at a target site of a malignancy by depositing an amount of radiant energy at the target site sufficient to damage the DNA of the malignant cells. Malignant cells at the target site suffering sufficient damage to their DNA die and are removed from the body by natural processes. However, radiation in a therapeutic radiation beam does not distinguish between healthy cells and malignant cells, and may damage healthy cells as well as malignant cells. As a result, therapeutic radiation beams generally have to be accurately configured and aimed at a target site of a malignancy to concentrate deposited radiant energy at the malignancy, and minimize deposition of radiant energy to surrounding healthy tissue.

For malignancies, such as malignancies in or on the appendages, or the brain, which may relatively easily be stabilized and kept stationary during radiation therapy, therapeutic radiation beams may generally effectively be configured to localize deposition of radiant energy to the malignancies. For malignancies located in or on an organ of the thoracic or abdominal regions of the body, such as malignancies of the left breast, lungs, liver, and pancreas, breathing may generate relatively large motion of the organ and thereby the malignancies. Maintaining a radiation beam focused on the moving malignancies may be a relatively complex and difficult undertaking.

A conventional procedure for depositing radiant energy by a therapeutic radiation beam to a malignancy exhibiting motion during irradiation may involve forming the beam sufficiently large so that the malignancy remains within the beam cross section throughout irradiation. To moderate exposure of healthy tissue during irradiation, a therapeutic radiation beam may be controlled to follow motion of the malignancy during irradiation. Alternatively or additionally, a therapeutic radiation beam may be shuttered on and off in synchrony with a patient's respiratory motion so that doses of radiation are delivered to the malignancy each time it moves through a same given location. In some procedures, attempts may be made to physically constrain a patient's respiratory motion during irradiation by pressing on the patient's abdomen to moderate motion of the malignancy due to respiration during irradiation.

SUMMARY

An aspect of an embodiment of the invention relates to providing apparatus, hereinafter also referred to as "Steady-Site", for performing a procedure at a target site in the thoracic or abdominal regions of a patient's body and constraining movement of the target site due to respiratory motion during the procedure. Steady-Site may comprise at least one or any combination of more than one of a diagnostic, interventional, and/or therapeutic device, to be delivered to the target site for performance of the procedure or for delivering an agent to the target site for performance of the procedure. Hereinafter a diagnostic, interventional, and/or therapeutic device in accordance with an embodiment of the invention may be generically referred to as a medical device. An agent may comprise a substance and/or energy for delivery to the target site. Steady-Site comprises apparatus for providing continuous positive airway pressure (CPAP) to the patient's lungs during the procedure to constrain motion of the target site, expand the chest cavity and lungs, and/or displace organs and tissue in the chest cavity to distance them from the target site.

A procedure performed at a target site, or treating a target site, may refer to any medical or imaging procedure that may be performed at, in, or of the site, or any combination of more than one of such procedures. In an embodiment of the invention the medical device may be a manually operated or deployed medical device or a robotic device that operates autonomously or semi-autonomously to deliver an agent to the target site and/or to deploy at the target site.

In an embodiment of the invention, Steady-Site may comprise a controller that controls delivery of the medical device and/or agent. Optionally, the controller controls the CPAP apparatus to provide CPAP during performance of the procedure. The CPAP provided during the procedure in accordance with an embodiment of the invention operates to flatten and reduce motion of the diaphragm during respiration, and expand the lungs and chest cavity. The CPAP thereby moderates motion of tissue and organs in the thoracic and abdominal regions due to patient respiration, and as a result, motion of the target site during irradiation. Expansion of the lungs and chest cavity tends to reposition and increase spacing between organs in the chest cavity and abdomen. The reduced motion of the target site and other organs and tissue in the thoracic and abdominal regions of the patient facilitates delivery of a medical device or agent to the target site and contributes to reduction of possible collateral damage to tissue outside of the target site resulting from delivery of the medical device or agent. Expansion of the lungs and chest cavity and resultant repositioning and spacing of organs in the chest and abdomen may also facilitate delivery of a medical device or agent to the target site and reduction of possible collateral damage to tissue outside of the target site resulting from delivery of the medical device or agent.

For example, CPAP administered in accordance with an embodiment of the invention, tends to displace the heart caudally relative to the left breast. As a result, the heart may benefit from reduced exposure to radiation in a radiation beam directed to deliver a dose of radiation to a target site comprising a malignant lesion of the left breast. Expansion of the lungs due to CPAP reduces density of lung tissue, which generally improves contrast between tissue in the target site and lung tissue for medical imaging modalities that might be used to acquire images of a target site in the thoracic region of a patient.

In an embodiment of the invention, a Steady-Site apparatus, which may be referred to as Steady-Site ACCURAD, or ACCURAD, is configured to provide radiation therapy and comprises radiation therapy equipment for delivering radiation to a target site of, optionally a malignancy, in the thoracic or abdominal regions of a patient's body with reduced exposure of healthy tissue in a neighborhood of the malignancy to the radiation. Steady-Site ACCURAD optionally comprises a radiation beam and a controller that controls the radiation beam, and the CPAP apparatus to provide CPAP during irradiation of the target site by the radiation beam. An ACCURAD therapeutic radiation beam may therefore generally be relatively accurately aimed at the malignancy and be configured having a smaller cross section perpendicular to its direction of propagation than therapeutic radiation beams provided by conventional radiation facilities. The ACCURAD therapeutic radiation beam is therefore generally able to deliver radiation to a target site of a malignancy with reduced collateral damage to healthy tissue An aspect of an embodiment of the invention relates to determining an internal target volume (ITV) for a malignancy of a patient to be irradiated by an ACCURAD radiation beam. An ITV for a malignancy is generally defined to include a clinical target volume (CTV) of the malignancy, which is a volume of tissue that contains a gross tumor volume (GTV) that characterizes the malignancy, as well as tissue peripheral to the GTV that is considered to require radiation therapy. The ITV is generally larger than the CTV and is defined as a volume that substantially contains, and within which the CTV may be predicted to move as a result of motion, generated for example by the patient's respiratory motion, of the malignancy during irradiation. In accordance with an embodiment of the invention, motion of the patient's malignancy is imaged, optionally using an MRI (magnetic resonance imaging) scanner and/or a CT (computed tomography) scanner, which may for example perform a 4D (four dimension) CT scan, PET/CT (positron emission tomography/CT)scan, or cone beam CT scan during provision of CPAP to the patient. The reduced motion of the malignancy, increased separation of organs, and improved tissue contrast resulting from the provision of CPAP enables determination of an ITV, hereinafter also referred to as a CPAP-ITV, for treating the malignancy with the ACCURAD radiation beam that is generally smaller than a conventional ITV.

In an embodiment of the invention ACCURAD may comprise a medical imager such as by way of example, an ultrasound, PET, MRI, or a CT scanner, and the ACCURAD controller controls the CPAP apparatus and the medical imager to acquire images of the malignancy and motion of the malignancy during provision of CPAP to determine the CPAP-ITV. Optionally, the controller comprises a computer executable instruction set for image processing the images to determine a GTV and CTV for the malignancy and/or for determining the CPAP-ITV.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the invention in a figure may be used to reference the given feature. Dimensions of features shown in the figures are chosen for convenience and clarity of presentation and are not necessarily shown to scale.

DETAILED DESCRIPTION

Figure 1A:
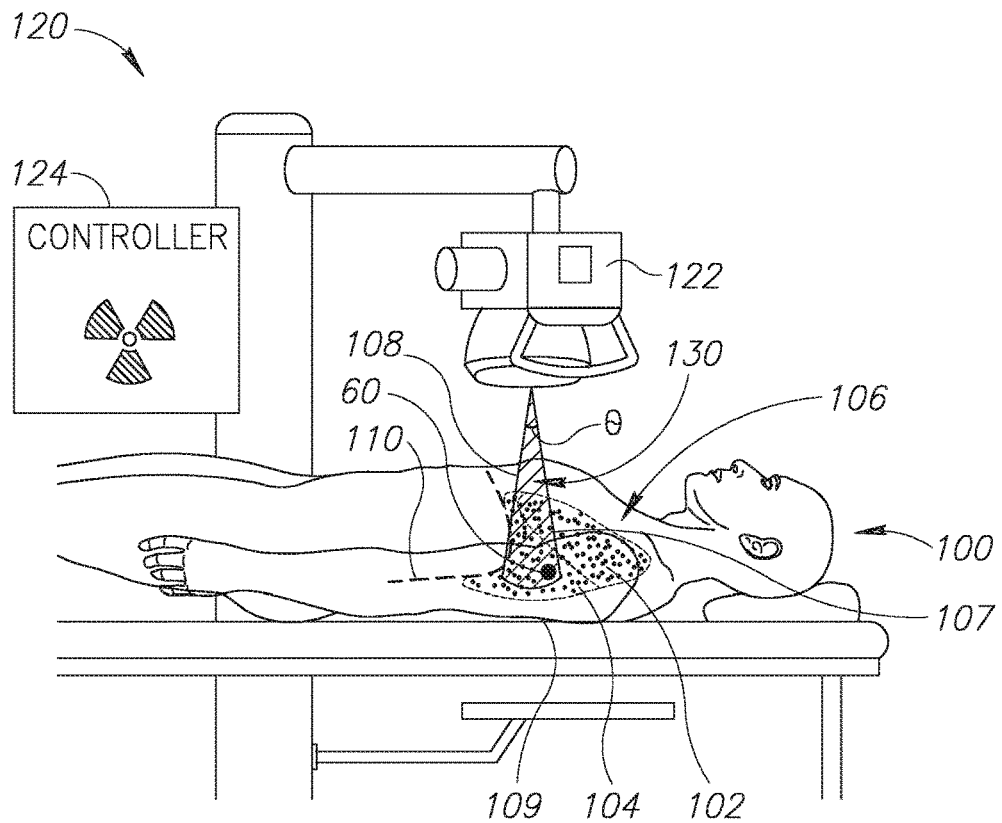
FIGS. 1A-1C schematically show treating a malignancy located in the thoracic cavity of a patient using a conventional therapeutic radiation beam apparatus.
Figure 1B:
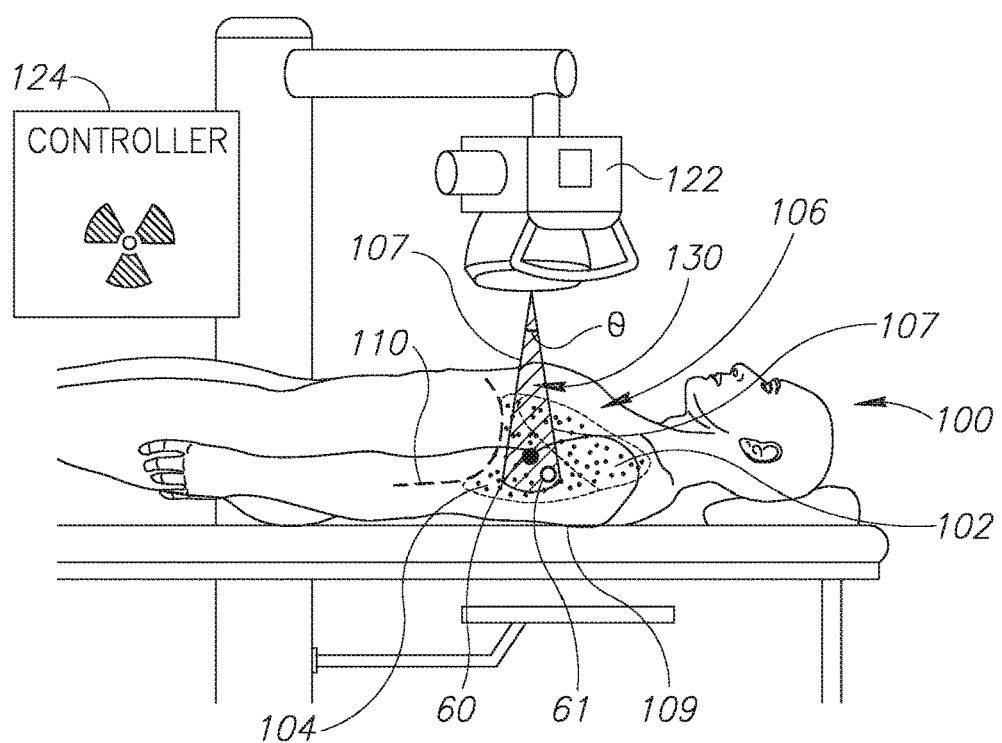
Figure 1C:
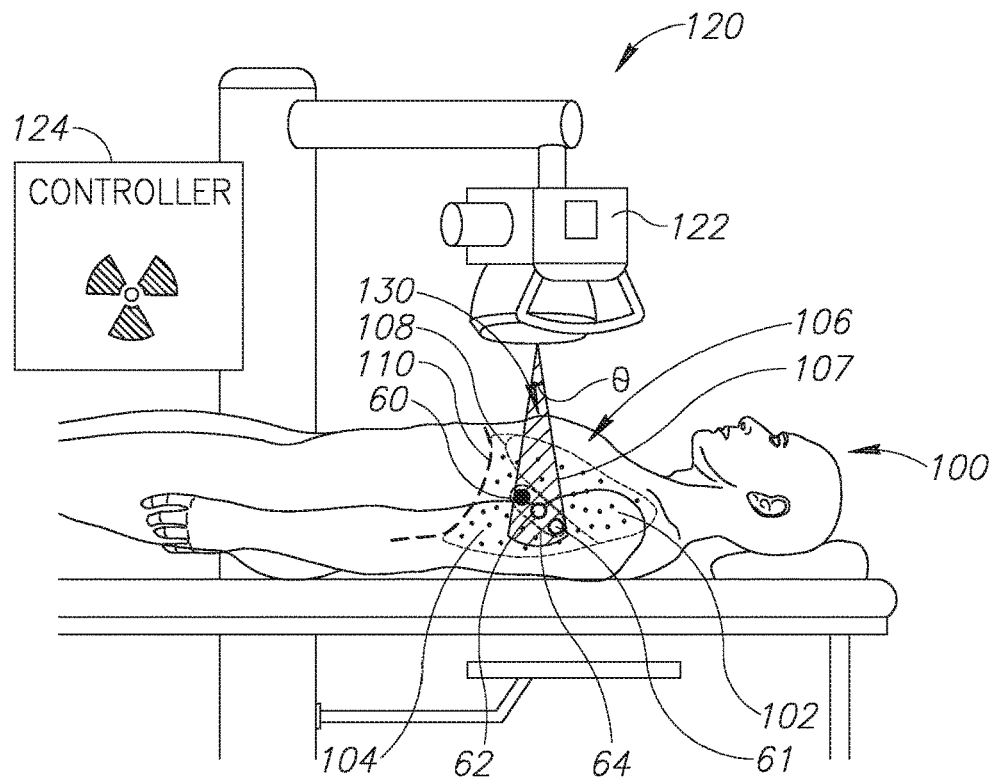
Figure 2:
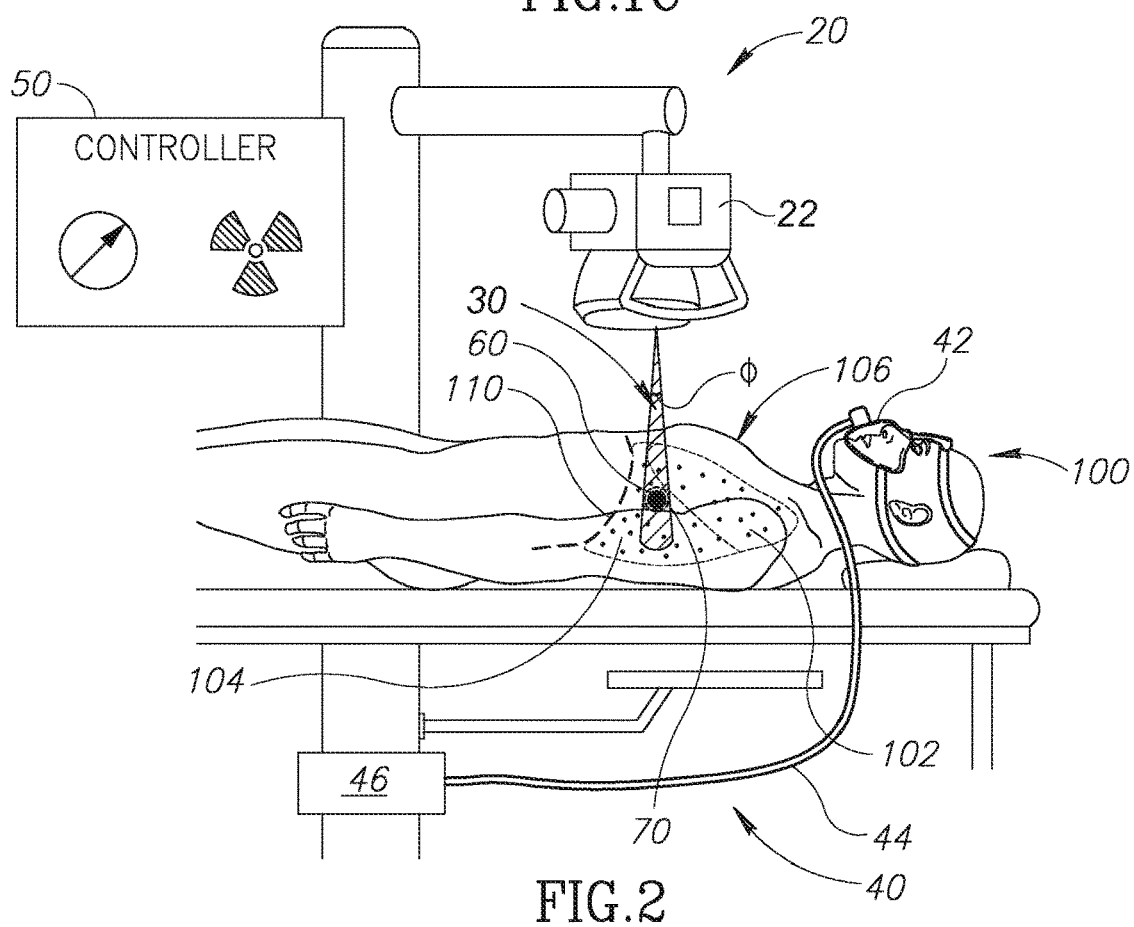
FIG. 2 schematically shows treating the malignancy shown in FIGS. 1A-1C using a Steady-Site ACCURAD apparatus, in accordance with an embodiment of the invention.
Figure 3:
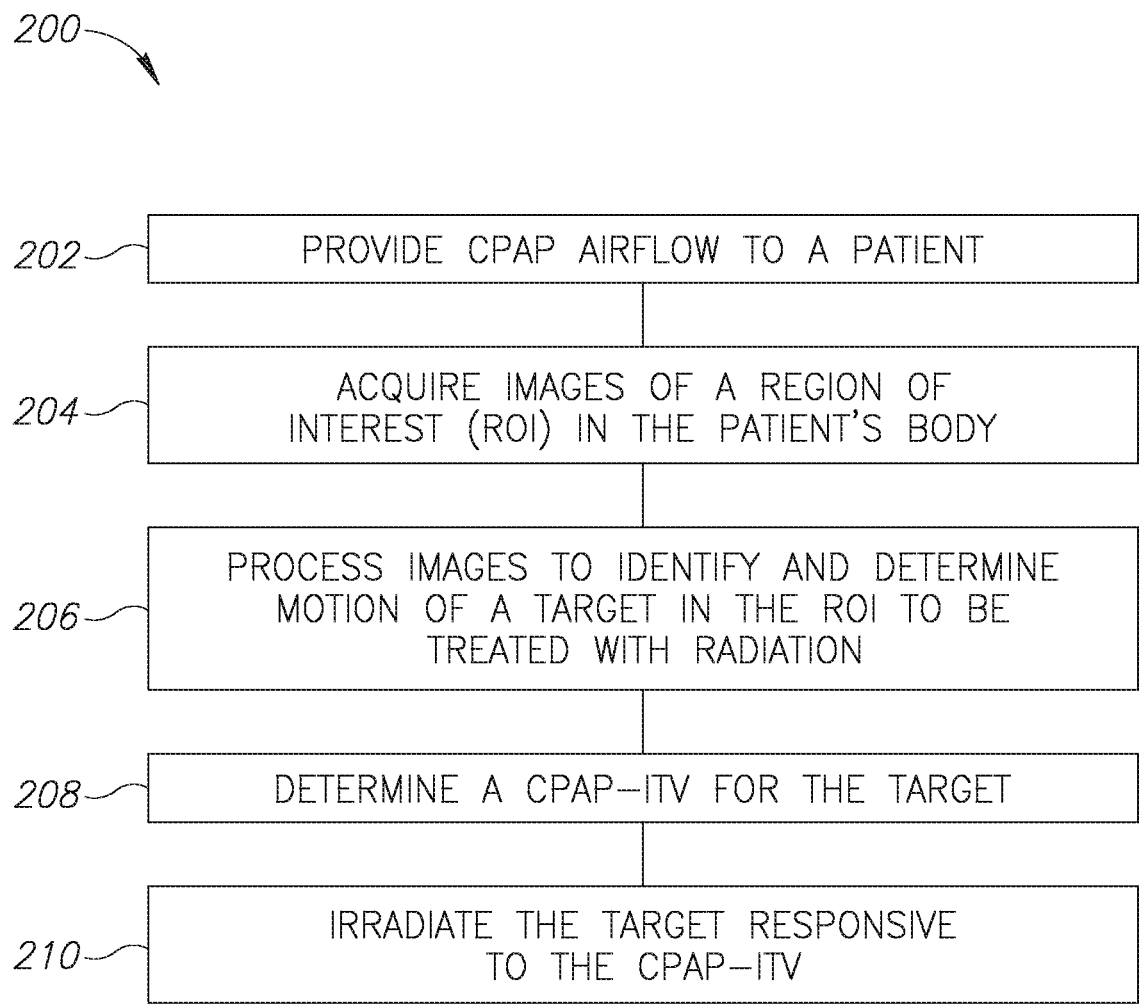
FIG. 3 shows a flow diagram of a procedure for treating a malignancy with an ACCURAD radiation beam, in accordance with an embodiment of the invention.

The following detailed description describes a conventional procedure, schematically illustrated in FIGS. 1A-1C for, by way of example, irradiating a malignant lesion of the left lower lung of a patient to deliver a therapeutically effective dose of radiation to the lesion. The illustrated conventional procedure shows movement of the lesion during irradiation due to respiratory motion of the lungs and diaphragm and resultant exposure of healthy tissue to radiation. FIG. 2 schematically shows a similar procedure performed on the same lesion by a Steady-Site ACCURAD apparatus in which motion of the lesion is moderated by CPAP, and a relatively narrow focused beam of radiation irradiates the lesion in accordance with an embodiment of the invention. The moderated motion of the lesion and narrow beam of radiation reduces exposure of healthy tissue surrounding the lesion to radiation. A flow diagram for a procedure for treating a target site, optionally malignant lesion, in accordance with an embodiment of the invention is shown in FIG. 3 and discussed with reference to the figure.

FIGS. 1A-1C schematically show a patient 100 being treated for a malignant lesion represented by a solid circle 60 by a conventional radiology machine 120. The size of solid circle 60 schematically represents a clinical target volume (CTV) determined for the lesion. In the figures, outer boundaries of left upper lobe (LUL) 102 and left lower lobe (LLL) 104 of the left lung in the patient's chest cavity 106, are indicted by fine dashed lines, and the patient's diaphragm 110 is shown in a bold dashed line. Lung tissue within the fine dashed lines outlining LUL 102 and LLL 104 is indicated by dotted shading. Density of lung tissue is schematically represented by density of the shading. By way of example, malignant lesion 60 is located on LLL 104.

Radiology machine 120 comprises a radiation beam generator 122 and a controller 124 that controls beam generator 122 to irradiate patient 100 with a radiation beam 130 having characteristics that are advantageous for delivering a desired dose of radiation to lesion 60 that may control and eradicate the lesion. The figures show radiology machine 120 irradiating patient 100 during a respiratory cycle. Optionally, radiation beam 130 is a beam of X-rays.

Lesion 60 undergoes substantial motion during respiration of patient 100, and radiation beam 130 is configured by controller 124 having a solid angle sufficiently large so that the lesion does not move outside of the beam at any time during the patient's respiratory cycle. In particular, a component of motion of lesion 60 during respiration of patient 100 parallel to the sagittal plane (not shown) of the patient's body is relatively large. The plane of FIGS. 1A-1C is parallel to the patient's sagittal plan and is assumed to intersect the trajectory of motion that lesion 60 executes during respiration. Therefore, to contain lesion 60 during respiration, controller 124 controls beam generator 122 to configure radiation beam 130 so that the radiation beam has a relatively large cross section defined by a relatively large opening angle θ in the plane of FIGS. 1A-1C.

In FIG. 1A, patient 100 has just completed exhaling, the patient's diaphragm 110 is maximally elevated into the chest cavity, to contract the chest cavity volume and compress lung volume substantially to their minimum, and patient 100 is about to initiate inhalation. As a result of the compressed lung volume, lung tissue density is substantially at a maximum, which is schematically indicated by relatively dense shading of LUL 102 and LLL 104. Lesion 60 is located high in the chest cavity near a lower right edge 107 of radiation beam 130.

In FIG. 1B patient 100 is inhaling and substantially in the middle of the inhalation portion of the patient's respiratory cycle. Diaphragm 110 is partially contracted to move the diaphragm inferiorly away from the chest cavity to expand and reduce pressure in the chest cavity and expand and draw air into the lungs. As a result of motion of diaphragm 110, associated expansion of chest cavity 106 and rib cage (not shown), and expansion of LUL 102 and LLL 104, lesion 60 has moved downward in the chest cavity and away from the back 109 of patient 100, to locate substantially along a midline (not shown) of radiation beam 130. Empty circle 61 in FIG. 1B indicates where lesion 60 was located at the earlier, full exhalation stage of the respiratory cycle of patient 100 shown in FIG. 1A. Density of shading of LUL 102 and LLL 104 is reduced in FIG. 1B relative to density of shading of LUL 102 and LLL 104 in FIG. 1 A to indicate that expansion of the lungs has reduced lung tissue density relative to lung tissue density at full exhalation.

FIG. 1C schematically shows patient 100 when the patient's respiration has progressed from the middle of the inhalation portion of the respiration cycle shown in FIG. 1B to a state at which the patient has fully inhaled. Diaphragm 110 is maximally contracted and drawn inferiorly to expand chest cavity 106 and the lungs to their respective maximum volumes and inspire air to fully fill the lungs. Density of lung tissue in the fully expanded lungs is substantially at a minimum and is schematically indicated by the relatively sparse shading of LUL 102 and LLL 104 in FIG. 1C. As a result of motion of diaphragm 110, associated motion of the rib cage and expansion LUL 102 and LLL 104, lesion 60 has displaced further downward in the chest cavity 106 and away from the back to a position along a left edge 108 of beam 130. In FIG. 1C open circles 61 and 62 indicate positions of lesion 60 at the earlier stages of the respiratory cycle of patient 100 shown respectively in FIGS. 1A and 1B.

Following full inhalation as shown in FIG. 1C, diaphragm 110 relaxes to retrace in reverse its motion shown in FIG. 1A to FIG. 1C and cause chest cavity to contract and expel air from the lungs in an exhalation portion of the respiratory cycle of patient 100. When fully relaxed, exhalation is complete, diaphragm 110 is returned to its fully elevated position in chest cavity 106 shown in FIG. 1A and patient 100 is ready again to initiate inhalation and begin a new respiratory cycle. During exhalation, in sympathy with motion of diaphragm 110 and contraction of chest cavity 106, lesion 60 reverses its motion and retraces its trajectory backwards to move from its location in FIG. 1C, through the location indicated by open circle 62, to the location of lesion 60 shown in FIG. 1A and indicated in FIG. 1C by open circle 61.

With each complete respiratory cycle, from initiation of inhalation through completion of exhalation, lesion 60 executes round trip motion from its location in FIG. 1A to its location in FIG. 1C and back to its location in FIG. 1A. A boundary 64 in FIG. 1C surrounds empty circles 61 and 62 and lesion 60 and encompasses the round trip trajectory of lesion 60. Boundary, 64 represents a boundary of an internal target volume, ITV, for lesion 60. Numeral 64 may be used to refer to the ITV bounded by boundary 64 as well as the boundary. The size of radiation beam 130 and the size of ITV 64 are substantially dictated by the size of the GTV of lesion 60 and a constraint to maintain the lesion within radiation beam 130 during the respiration cycle of patient 100. The size of radiation beam 130 and the size of ITV 64 in FIGS. 1A-1C indicates that in addition to the GTV of lesion 60, a substantial volume of the patient's healthy tissue is exposed to potentially damaging radiation during treatment.

FIG. 2 schematically shows a Steady-Site ACCURAD apparatus 20 for providing radiation therapy, in accordance with an embodiment of the invention. In the figure ACCURAD 20 is schematically shown treating patient 100 for the same lesion 60 of LLL 104 shown in FIGS. 1A-1C.

Steady-Site ACCURAD 20 optionally comprises a radiation beam generator 22, a CPAP apparatus 40, and a controller 50 that controls the radiation beam generator and the CPAP apparatus. CPAP apparatus 40 optionally comprises a face mask 42, shown mounted to the face of patient 100 and connected by a flow tube 44 to an air pump system 46. The air pump system is controllable by controller 50 to provide a flow of breathable gas such as air at a desired pressure and flow rate to the face mask and thereby to patient 100 via flow tube 44. Optionally, CPAP apparatus 40 is controllable to provide a flow of gas to face mask 42 other than a conventional mix of gases found in air. For example, controller 50 may control air pump system 46, in accordance with an embodiment of the invention, to provide a mix of gases to face mask 42 having higher or lower oxygen content than ambient air. Optionally, controller 50 controls air pump system 46 to provide a desired humidity and/or temperature of gases that flows to face mask 42. Gas flow under any suitable condition of pressure, flow rate, temperature and humidity, and any suitable mix of gases provided to a patient, such as patient 100, by a CPAP apparatus in accordance with an embodiment of the invention, may be referred to a CPAP gas flow or CPAP airflow.

To provide a desired dose of radiation to lesion 60, controller 124 controls CPAP apparatus 40 to provide an optionally constant CPAP gas flow of air to face mask 42 at a pressure and flow rate sufficient to substantially fully expand the lungs of patient 100 and moderate motion and position of diaphragm 110, the lungs, and other internal organs of the patient's chest cavity, and thereby motion of lesion 60, during respiration. The fully expanded lungs have a relatively low lung tissue density that may be substantially equal to the low lung tissue density represented in FIG. 1C. The low lung tissue density is indicated in FIG. 2 by the density of shading of LUL 102 and LLL 104, which is the same as the density of shading of LUL 102 and LLL 104 in FIG. 1C.

Following initiation of CPAP airflow to patient 100, controller 50 controls beam generator 22 to generate a beam 30 of radiation that is aimed at lesion 60. Since provision of the CPAP airflow in accordance with an embodiment of the invention moderates motion of lesion 60, the lesion is associated with an ITV, a "CPAP-ITV", schematically indicated by a border 70, that is smaller than ITV 64 associated with lesion 60 (FIG. 1C) when the lesion is treated by a conventional radiology machine such as radiology machine 120 (FIGS. 1A-1C). As a result, radiation beam 30 provided by Steady-Site ACCURAD 20 in accordance with an embodiment of the invention, may be characterized by a solid angle that is relatively small compared to the solid angle of beam 130. Therefore, as schematically shown in the plane of FIG. 2, radiation beam 30 generated by Steady-Site ACCURAD 20 to treat lesion 60 has an opening angle $\varphi$ relatively small compared to the opening angle $\theta$ of radiation beam 130 (FIGS. 1A-1C) generated by conventional radiology machine 120.

As a result of its relatively small solid angle, a volume of healthy tissue in patient 100 that is exposed to potentially damaging radiation from ACCURAD radiation beam 30 provided by Steady-Site ACCURAD 20 is relatively small compared to a volume of healthy tissue exposed to radiation from conventional radiation beam 130.

By way of a numerical example, conventional X-ray radiation machine 120 may irradiate a lesion 60 with radiation beam 130 of X-rays (FIG. 1A-1C) from a distance of about 100 cm (centimeter). The lesion may have a determined ITV 64 characterized by maximum dimension equal to about 10 cm perpendicular to a direction of propagation of X-ray beam 130. The X-ray beam may therefore have an angle $\theta$ ( ) in the plane of FIGS. 1A-1C equal to about 5.7°. For the same lesion 60, CPAP-ITV 70 determined for Steady-Site ACCURAD radiation machine 20 (FIG. 2) may have a maximum dimension perpendicular to ACCURAD radiation beam 30 provided by ACCURAD equal to about 7 cm. In the plane of FIG. 2, ACCURAD radiation beam 30 may therefore have an angle $\varphi$ (FIG. 2) equal to about 4.0°.

In an embodiment of the invention, a Steady-Site ACCURAD apparatus, similar to ACCURAD 20, comprises a medical imager (not shown) operable to image, an optionally malignant, lesion of a patient to be treated by ACCURAD. The imager may use any of various suitable medical imaging modalities to image the lesion. By way of example, the medical imager may image the lesion using one, or any combination of more than one of MRI (magnetic resonance imaging), flouroscopy, CT (computed tomography), PET (positron emission spectroscopy), SPECT (single photon emission computed tomography), or ultrasound scanners. ACCURAD may operate the medical imager to image the lesion while controller 124 controls CPAP apparatus 40 to provide CPAP airflow to the patient that expands the patient's lungs and moderates motion of the patient's diaphragm, and the lesion. A processor optionally comprised in controller 124 processes the images to identify the lesion and determine the moderated motion of the lesion during provision of CPAP airflow to the patient. The processor may determine a CPAP-ITV, for example CPAP-ITV 70 shown in FIG. 2, that is used to configure a beam of radiation for treating the lesion, responsive to the identified lesion and imaged moderated motion.

FIG. 3 presents a flow diagram 200 of simplified procedure in accordance with which a Steady-Site ACCURAD apparatus may operate to deliver therapeutic radiation to a target site of a patient's body.

In a block 202 Steady-Site ACCURAD 20 provides CPAP airflow to the patient. Optionally in a block 204 while the patient is experiencing CPAP airflow Steady-Site ACCURAD acquires images of a region of interest (ROI) in the patient's body. In a block 206 the images are processed to identify a target site in the ROI to be treated with radiation provided by Steady-Site ACCURAD and determine motion of the target site during respiration. Optionally in a block 208 a CPAP-ITV is determined for the target site and in a block 210 the target site is irradiated with radiation provided by Steady-Site ACCURAD responsive to the CPAP-ITV.

Whereas in the above description radiation beam 30 provided by ACCURAD 20 may be considered by omission as being a static beam that is substantially unchanged during irradiation of lesion 60, practice of an embodiment of the invention is not limited to static radiation beams. For example, an ACCURAD radiation beam may be shuttered in synchrony with motion of a lesion within a CPAP-ITV to irradiate the lesion at a same location within the CPAP-ITV substantially only when the lesion moves through the location. Alternatively or additionally, an ACCURAD radiation beam may be controlled to track a lesion during its motion within a CPAP-ITV.

The above description describes irradiating a lesion during provision of CPAP airflow and imaging a patient's lesion using any of various imaging modalities and CPAP airflow. However, practice of an embodiment of the invention is not limited to therapeutic radiology or medical imaging of lesions. A Steady-Site apparatus in accordance with an embodiment of the invention may for example be used to stabilize a tissue in a target site in a patient's body to facilitate performing a biopsy of tissue in the target site, or to carry out radiofrequency or MRI focused ultrasound ablation of tissue in the target site. A Steady-Site apparatus may be advantageous for use in stabilizing an organ during a medical procedure such as by way of example, stabilizing heart motion during valve replacement or catheterization of the heart or catheterization and/or stent deployment of blood vessels in or connected to the heart. Generally catheterization of a target site, such as the heart or a blood vessel is preformed while imaging the target site. Providing CPAP during catheterization, as noted above, may improve resolution of the imaging by reducing motion of the target site, increasing distance of the target site from adjacent organs, and/or increasing contrast of the target site relative to surrounding tissue. The improved resolution may enable reduction of a radiation dose and/or a quantity of contrast or isotope to which the patient may be exposed to effect the imaging.

There is therefore provided in accordance with an embodiment of the invention, apparatus for performing a procedure at a target site of a patient's body, the apparatus comprising: a continuous positive airway pressure (CPAP) apparatus that provides CPAP to the patient's lungs; a medical device for performing the procedure at the target site; and a controller that controls the CPAP apparatus to provide CPAP to the patient's lungs during performance of the procedure. Optionally, the medical device comprises a radiation beam generator that generates a radiation beam for irradiating tissue at the target. Optionally, the radiation beam generator configures the radiation beam to irradiate an internal target volume (ITV) in the patient's body that comprises the target site. The ITV may be determined responsive to an image of the target site acquired by a medical imager during provision of CPAP to the patient's lungs. The apparatus may comprise a medical imager that acquires the image of the target site. The controller optionally comprises an executable instruction set that the controller executes to process the image to determine the ITV.

In an embodiment of the invention, the medical device comprises a tissue ablator that delivers energy to tissue in the target site to ablate the tissue.

In an embodiment of the invention, the medical device comprises a biopsy sampler that operates to acquire a sample of tissue in the target site.

In an embodiment of the invention, the medical device comprises a catheter.

In an embodiment of the invention, the medical device comprises a stent.

In an embodiment of the invention, the medical device comprises a medical imager.

In an embodiment of the invention, the medical device comprises a robotic device controlled by the controller.

In an embodiment of the invention, the medical device comprises a manually operated medical device.

There is further provided in accordance with an embodiment of the invention method of performing a procedure at a target site of a patient's body, the method comprising: providing continuous positive airway pressure (CPAP) to the patient's lungs; and performing the procedure at the target site during provision of CPAP to the patient's lungs.

Optionally, the procedure comprises irradiating the target site with radiation. Optionally, the method comprises determining an internal target volume (ITV) for the target site that is illuminated by the radiation. Optionally, determining the ITV comprises acquiring an image of the target site during provision of CPAP to the patient's lungs and determining the ITV responsive to the image.

In an embodiment of the invention, the procedure comprises performing a biopsy of tissues at the target site. In an embodiment of the invention, the procedure comprises ablating tissue at the target site. In an embodiment of the invention, the procedure comprises imaging tissue at the target site. In an embodiment of the invention, the procedure comprises catheterizing the target site In an embodiment of the invention, the procedure comprises performing a biopsy of tissues at the target site. In an embodiment of the invention, the procedure comprises ablating tissue at the target site. In an embodiment of the invention, the procedure comprises imaging tissue at the target site. In an embodiment of the invention, the procedure comprises catheterizing the target site.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. Apparatus for performing a procedure at a target site of a patient's body, the apparatus comprising:
   a continuous positive airway pressure (CPAP) apparatus adapted to provide CPAP to the patient's lungs;
   a medical device adapted to perform the procedure at the target site; and
   a controller configured to control the CPAP apparatus based on images provided by a medical imager to provide CPAP to the patient's lungs at a pressure and flow rate that maintains the lungs substantially fully expanded to moderate motion of the target site during performance of the procedure and determining a desired internal target volume (ITV);
   wherein the procedure and maintenance of the lungs substantially fully expanded lasts for a period of time equal to or greater than about a complete breathing cycle of the patient and during the period of time provision of CPAP to the lungs is not synchronized with the patient's breathing cycle.

2. The apparatus according to claim 1 wherein the medical device comprises a radiation beam generator that generates a radiation beam for irradiating tissue at the target site.

3. The apparatus according to claim 2 wherein the radiation beam generator configures the radiation beam to irradiate the internal target volume (ITV) in the patient's body that comprises the target site.

4. The apparatus according to claim 3 and comprising the medical imager operable to provide the images of the target site.

5. The apparatus according to claim 4 wherein the controller comprises an executable instruction set that the controller executes to process the images to determine the ITV.

6. The apparatus according to claim 1 wherein the medical device comprises a tissue ablator adapted to deliver energy to tissue in the target site to ablate the tissue.

7. The apparatus according to claim 1 wherein the medical device comprises a biopsy sampler that is adapted to acquire a sample of tissue in the target site.

8. The apparatus according to claim 1 wherein the medical device comprises a catheter for cardiac catheterization.

9. The apparatus according to claim 1 wherein the medical device comprises a stent.

10. The apparatus according to claim 1 wherein the medical device comprises the medical imager operable to provide the images of the target site on which the controller bases control of the CPAP apparatus.

11. The apparatus according to claim 1 wherein the medical device comprises a robotic device controlled by the controller.

12. The apparatus according to claim 1 wherein the medical device comprises a manually operated medical device.

* * * * *